(12) United States Patent
Moon

(10) Patent No.: US 9,814,877 B2
(45) Date of Patent: Nov. 14, 2017

(54) BIOSIGNAL MEASUREMENT AND ELECTRICAL STIMULATION DEVICE USING MESH STRUCTURE

(71) Applicant: Smart Medical Device Co., Ltd., Goyang (KR)

(72) Inventor: Changon Moon, Goyang (KR)

(73) Assignee: SMART MEDICAL DEVICE CO., LTD., Goyang-Si (KR)

( * ) Notice: Subject to any disclaimer, the term of this patent is extended or adjusted under 35 U.S.C. 154(b) by 0 days.

(21) Appl. No.: 14/773,800

(22) PCT Filed: Nov. 13, 2014

(86) PCT No.: PCT/KR2014/010918
§ 371 (c)(1),
(2) Date: Sep. 9, 2015

(87) PCT Pub. No.: WO2015/080409
PCT Pub. Date: Jun. 4, 2015

(65) Prior Publication Data
US 2016/0256686 A1    Sep. 8, 2016

(30) Foreign Application Priority Data

Nov. 29, 2013  (KR) .................. 10-2013-0147685
Jan. 13, 2014   (KR) .................. 10-2014-0004092

(51) Int. Cl.
*A61N 1/18*  (2006.01)
*A61N 1/36*  (2006.01)
(Continued)

(52) U.S. Cl.
CPC .......... *A61N 1/36014* (2013.01); *A61B 5/053* (2013.01); *A61N 1/0452* (2013.01);
(Continued)

(58) Field of Classification Search
CPC .............. A61N 1/36014; A61N 1/0476; A61N 1/0492; A61B 2562/046
See application file for complete search history.

(56) References Cited

U.S. PATENT DOCUMENTS 6,301,500 B1 * 10/2001 Van Herk ............ A61B 5/0531
600/393
7,945,302 B2 * 5/2011 McAdams ........... A61B 5/0531
600/382
(Continued)

FOREIGN PATENT DOCUMENTS

JP    2004-129699    4/2004
JP    2009-502399    1/2009
(Continued)

OTHER PUBLICATIONS

EPO, The European Search report,European Patent Application No. 14866781.9, dated Apr. 7, 2017.

*Primary Examiner* — George Evanisko
(74) *Attorney, Agent, or Firm* — Lex IP Meister, PLLC

(57) ABSTRACT

A bio-electrical signal measurement and electrical stimulation device using skin resistance is provided. The biosignal measurement and electrical stimulation device includes: a pad in which a plurality of horizontal electrical wires and vertical electrical wires for electrical stimulation are formed to intersect at a constant gap; and a control module that is electrically connected to the pad to acquire body information of a patient by measuring a biosignal of intersections in which the horizontal electrical wires and the vertical electrical wires intersect and that enables generation of electrical stimulation while controlling power that is supplied to the horizontal electrical wires and the vertical electrical wires using the body information.

9 Claims, 9 Drawing Sheets

(51) Int. Cl.
*A61B 5/053* (2006.01)
*A61N 1/04* (2006.01)

(52) U.S. Cl.
CPC ......... *A61N 1/0456* (2013.01); *A61N 1/0476* (2013.01); *A61N 1/0484* (2013.01); *A61N 1/0492* (2013.01); *A61B 2562/046* (2013.01)

(56) References Cited

U.S. PATENT DOCUMENTS

| | | | |
|---|---|---|---|
| 8,145,318 B2* | 3/2012 | Van Herk | A61N 1/0452 607/48 |
| 2008/0262569 A1 | 10/2008 | Greenberg | |
| 2011/0071419 A1 | 3/2011 | Liu | |
| 2012/0146797 A1 | 6/2012 | Oskin et al. | |
| 2012/0226130 A1 | 9/2012 | De Graff | |
| 2013/0023781 A1 | 1/2013 | Freeman | |
| 2013/0072775 A1 | 3/2013 | Rogers | |

FOREIGN PATENT DOCUMENTS

| | | |
|---|---|---|
| JP | 2010-505465 | 2/2010 |
| JP | 4425428 | 3/2010 |
| JP | 2010-512827 | 4/2010 |
| JP | 2013-509905 | 3/2013 |
| JP | 2013-511321 | 4/2013 |
| JP | 2013-526371 | 6/2013 |
| JP | 5623628 | 11/2014 |
| JP | 2014-533160 | 12/2014 |
| KR | 10-2013-0083350 | 7/2013 |
| WO | 98-56455 | 12/1998 |
| WO | 99-52588 | 10/1999 |
| WO | 2004/049937 | 6/2004 |
| WO | 2008/075250 | 6/2008 |
| WO | 2009-153730 | 12/2009 |
| WO | 2013/072368 | 5/2013 |

* cited by examiner

BIOSIGNAL MEASUREMENT AND ELECTRICAL STIMULATION DEVICE USING MESH STRUCTURE

TECHNICAL FIELD

The present invention relates to an electrical stimulation device using skin resistance. More particularly, the present invention relates to an electrical stimulation device that measures skin resistance of a patient, a voltage, a current value, and a waveform thereof using a pad in which horizontal electrical wires and vertical electrical wires are formed and that acquires body information from measured values and generates electrical stimulation using the acquired body information.

BACKGROUND ART

There are instruments that search for a treatment point by specifying a resistance value of a skin together with an existing electromyogram measurement mechanism and nerve conduction measurement mechanism. Further, there are mechanisms that induce a treatment effect by applying electrical stimulation to the treatment point.

When measuring electromyogram and nerve conduction, a measurement point for measuring a waveform according to a conduction speed of a nerve and measuring an activation potential of a muscle may be obtained through an operator's experience and anatomical knowledge and thus it is difficult for a non-medical expert to search for the measurement point, and when measuring a measurement point, a method of measuring one or two points and again measuring other points instead of simultaneously measuring several portions has been used.

When performing an electrical stimulation treatment, upon applying stimulation to a treatment point, a wide conductive pad that attaches to skin applies stimulation to the inside of the skin through a dry needle (electric needle), a limitation exists in stimulating an accurate location.

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide an electrical stimulation device having advantages of being capable of performing measurement and stimulation with a corresponding pad without separate equipment by searching for an accurate local portion for stimulation by measuring a biosignal of a body portion of a patient without separate medical knowledge and simultaneously performing measurement in several portions.

Technical Solution

An exemplary embodiment of the present invention provides a biosignal measurement and electrical stimulation device including: a pad in which a plurality of horizontal electrical wires and vertical electrical wires for electrical stimulation are formed to intersect; and a control module that is electrically connected to the pad to acquire body information of a patient by measuring a biosignal of intersections in which the horizontal electrical wires and the vertical electrical wires intersect and that enables generation of electrical stimulation while controlling power that is supplied to the horizontal electrical wires and the vertical electrical wires using the body information. An exemplary embodiment of the present invention provides a biosignal measurement and electrical stimulation device including: a pad in which a plurality of horizontal electrical wires and vertical electrical wires for electrical stimulation are formed to intersect; and a control module that is electrically connected to the pad to acquire body information of a patient by measuring a biosignal of intersections in which the horizontal electrical wires and the vertical electrical wires intersect and that enables generation of electrical stimulation while controlling power that is supplied to the horizontal electrical wires and the vertical electrical wires using the body information.

The control module may measure an electrical signal flowing to the intersection.

In a biosignal measurement and electrical stimulation device according to a first exemplary embodiment of the present invention, the horizontal electrical wires and the vertical electrical wires may be disposed to have a constant gap at intersections thereof, and the control module may measure a biosignal or generate electrical stimulation by enabling a current to flow by generating a predetermined potential difference between the horizontal electrical wires and the vertical electrical wires that are connected to the desired intersections.

In a biosignal measurement and electrical stimulation device according to a second exemplary embodiment of the present invention, a semiconductor element may be disposed between the horizontal electrical wire and the vertical electrical wire, and the control module may control the semiconductor element to measure a biosignal or to generate electrical stimulation at the intersection by flowing a current at the desired intersection.

In both exemplary embodiments, the intersection portion may be formed with an electrode or a bonding gel for an electrode, which is a conductor, and a periphery of the intersection may be formed with bonded fabric or bonding gel, which is an insulator.

In a biosignal measurement and electrical stimulation device according to a first exemplary embodiment of the present invention, at the intersection, the horizontal electrical wire and the vertical electrical wire may be insulated by an insulating material, and at the gap, a conductive material for reducing resistance when generating the electrical stimulation may be further provided.

In the pad, a perforated portion for air permeability may be formed.

The pad may have one of a circular shape, an oval shape, a square shape, a rectangular shape, a glove shape, a sock shape, a cap shape, a band shape, and a clothing shape.

The biosignal may represent skin resistance, and the control module may calculate a first average value of skin resistance of the intersection, set intersections having skin resistance of the first average value or less to a reference point among the intersections, calculate a second average value of skin resistance at the reference point, determine reference points having skin resistance of the second average value or less to a treatment point among the reference points, and generate electrical stimulation at the treatment point. The control module may stop electrical stimulation at a corresponding treatment point when a skin resistance value at the treatment point arrives at the second average value.

The biosignal may be an electrical signal, and the control module may calculate a standard deviation of an electrical signal measurement value of the intersection, determine a treatment point using an electrical signal measurement value of the remaining points except for the electrical signal measurement values that are deviated from a predetermined threshold when the electrical signal measurement value deviates from the predetermined threshold value, and generate electrical stimulation at the treatment point.

The biosignal may be an electrical signal, and the control module may search for a portion in which a change amount of an electrical signal of a muscle and an electrical signal of a nerve is a predetermined threshold value or more in a specific operation of a patient and generate electrical stimulation for muscular contraction in a corresponding portion.

The biosignal may be an electrical signal, the control module may apply sequential electrical stimulation to an intersection in order to search for an electrical stimulation portion of a muscle and nerve that cause a signal similar to each muscle electrical signal and nerve electrical signal of a specific operation of a patient, search for a muscle contraction causing point and a nerve stimulation causing point, and control to cause muscular contraction for a specific operation by applying electrical stimulation to the causing point.

Advantageous Effects

According to the present invention, a biosignal can be acquired from a measurement value such as impedance, a voltage, and a current value of each body portion, and a waveform thereof without knowledge of a corresponding field, and by applying electrical stimulation to a body portion using the acquired biosignal, a treatment can be effectively performed.

Further, according to the present invention, by enhancing inconvenience of an existing device that searches for an accurate body point, that measures a biosignal, and that applies electrical stimulation, a biosignal of several points can be simultaneously measured by attaching a pad to a body portion and electrical stimulation can be simultaneously or sequentially applied with the same pad.

Further, according to the present invention, as a plurality of horizontal electrical wires and vertical electrical wires are disposed, electrical stimulation can be simultaneously applied to several coordinates, a coordinate of a treatment portion can be automatically set, and by automatically changing an electrical stimulation coordinate according to a treatment level, a treatment can be effectively performed.

Further, according to the present invention, by using a pad of a form corresponding to a body portion of each patient, the pad can be easily detachably attached to the body portion in daily life, and a treatment can be easily performed.

MODE FOR INVENTION

Figure 1:
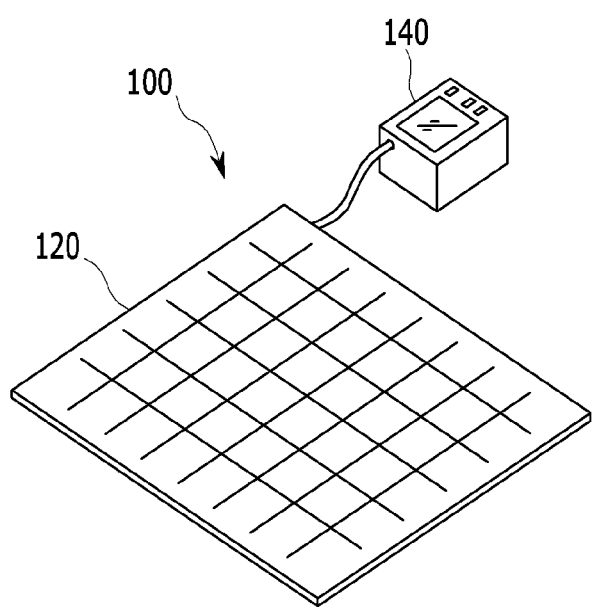
FIG. 1 is a perspective view illustrating an electrical stimulation device according to an exemplary embodiment of the present invention.

Hereinafter, an exemplary embodiment of the present invention will be described in detail with reference to the accompanying drawings.

Exemplary embodiments of the present invention are provided to further completely describe the present invention to a person of ordinary skill in the art, and the following exemplary embodiments may be changed in several different forms, and hereinafter, an exemplary embodiment of the present invention will be described in detail with reference to the accompanying drawings.

Exemplary embodiments of the present invention are provided to further completely describe the present invention to a person of ordinary skill in the art, the following exemplary embodiments may be changed in several different forms, and the scope of the present invention is not limited to the following exemplary embodiments. These exemplary embodiments enable to further complete the present disclosure, and are provided to completely transfer the spirit of the present invention to a person of ordinary skill in the art.

Terms used in this specification are used for describing a specific exemplary embodiment and do not limit the present invention. As used in this specification, a singular form may include a multiple form unless phrases explicitly represent a different case. A meaning of "comprise" and/or "comprising" used in a specification specifies presence of a described shape, numeral, step, operation, member, element, and/or a group thereof, and does not exclude presence or addition of at least another shape, numeral, operation, member, element, and/or a group thereof. As used in this specification, a term "and/or" includes any one and at least one entire combination among corresponding listed items.

In this specification, term "first" and "second" are used for describing various members, areas, and/or portions, but these members, components, areas, layers, and/or portions should not be limited by these terms. These terms do not mean a specific order, a vertical relationship, or superiority, and are used for distinguishing one member, area, or portion from another member, area, or portion. Therefore, a first member, area, or portion described hereinafter may indicate a second member, area, or portion without deviating from teaching of the present invention.

Hereinafter, exemplary embodiments of the present invention will be described with reference to the drawings. In the drawings, a shown shape may be changed according to, for example, production technology and/or tolerance. Therefore, an exemplary embodiment of the present invention is not limited to a specific shape of an area shown in this specification, and should include, for example, a change of a shape that may occur during production.

FIG. 1 is a perspective view illustrating an electrical stimulation device according to an exemplary embodiment of the present invention.

Referring to FIG. 1, a biosignal measurement and electrical stimulation device 100 according to an exemplary embodiment of the present invention includes a pad 120 and a control module 140.

The pad 120 is made of a buffer material such as silicon and urethane, and horizontal electrical wires and vertical electrical wires are disposed to intersect in the pad with a predetermined gap therebetween.

In FIG. 1, the pad 120 is formed in a quadrangular shape, but may be formed in various shapes such as a circular shape, an oval shape, a square shape, a rectangular shape, a sock shape, a glove shape, a cap shape, a band shape, and a clothing shape, and a perforated portion for air permeability may be formed in the pad 120. In this case, a sock shape is a form that is worn in a foot of a patient, and a glove shape is a form that is worn in a hand of a patient. Such a form of pad 120 contacts a specific body portion of a patient to be used.

The control module 140 is connected to the pad 120 through a cable, and by applying power of a current and a voltage to the pad 120, the control module 140 measures a biosignal of a body portion of a patient through the pad 120, acquires body information of the patient using the measured biosignal, and generates electrical stimulation in the body portion of the patient based on the acquired body information. In this case, a bio-electrical signal may represent skin resistance, a voltage, a current value, and waveform information thereof. In a biosignal measurement and electrical stimulation device according to a first exemplary embodiment of the present invention, when a treatment portion to be a treatment target is determined from body information, in order to apply electrical stimulation of a low frequency or a high frequency to the treatment portion, a switch is turned on so that electricity of a positive (+) electrode and a negative (−) electrode flows to a horizontal electrical wire and a vertical electrical wire of each coordinate, and electrical stimulation occurs. In this case, strongest electrical stimulation is applied to an intersecting portion of two electrical wires, which are a location most adjacent to a positive (+) electrode and a negative (−) electrode, and this is because strength of stimulation is gradually weakened due to increase of electrical resistance as a distance increases from an intersection of two electrical wires. Therefore, at an intersection of horizontal electrical wires and vertical electrical wires, strongest electrical stimulation occurs to perform a treatment operation.

With such a method, the control module 140 may apply electrical stimulation to all of a plurality of intersections in which horizontal electrical wires and vertical electrical wires that are formed in the pad 120 intersect or may selectively apply electrical stimulation to a portion thereof.

Further, a biosignal measurement and electrical stimulation device according to a first exemplary embodiment of the present invention may apply a biosignal and stimulation with a structure that can control through a switch function of each coordinate through current application of an emitter using a PNP-type transistor 30.

A biosignal measurement and electrical stimulation device according to first and second exemplary embodiments of the present invention will be described in detail with reference to FIGS. 2 to 7.

Further, in addition to the above method, a method of disposing each electrode at a skin bond surface of a pad and an external ground electrode at a circumferential surface of the pad and forming in one unit that directly connects and controls the electrodes to an input and output port (I/O port) may be used. In this case, the number of units may be appropriately increased or decreased according to a range of a biosignal measurement or electrical stimulation target.

In the present invention, electromyogram, nerve conduction, electrocardiogram, electroencephalogram, and functional electrical stimulation techniques may be used, and the present invention can be applied to a treatment according to Korean traditional medicine through a needle treatment point search and a probe.

Specifically, electromyogram (EMG) and nerve conduction velocity (NCV) are used to analyze body information of a patient by applying electrical stimulation to a muscle system and a nerve system and analyzing a measured signal, and functional electrical stimulation (FES) is a treatment operation that recovers an originally given function by applying electrical stimulation to a paralyzed muscle. It uses substantially the same principle to grasp body information of a patient and to apply electrical stimulation by analyzing a signal according to such electrical stimulation in a needle treatment point search and a probe of Korean traditional medicine or modern medicine.

In a nerve conduction test, in order to apply electrical stimulation to, for example, a finger and to measure nerve conduction, a sense nerve test is used to extract an electrical signal that appears while a nerve is activated by electrical stimulation from an electrode that is attached to a portion through which the nerve passes, and for a nerve conduction test of several nerves in a specific portion of an arm or a leg, a test should be performed several times at each nerve conduction path.

Upon using the present invention, when a start point of a line that is estimated as a nerve conduction path of a human body among coordinates of the pad is determined as a coordinate of an electrical stimulation electrode for determining nerve conduction, when electrical stimulation is applied to the start point, and when electrical stimulation is applied to the electrode coordinate, it is measured whether a signal corresponding to nerve conduction such as a predetermined waveform and a magnitude of a current and a voltage appearing when conducting a nerve is extracted at other coordinate, For example, when measuring from a wrist to an elbow of an arm, electrical stimulation is sequentially applied to each coordinate of a circumference of the wrist, and at a coordinate of an elbow portion, an electrical signal is extracted. In this case, for each nerve of a median nerve, a radial nerve, and an ulnar nerve, which are nerves from the wrist to the elbow, an existing nerve conduction tester should perform a test three times, and a test should be performed again when a measurement point is not accurate, but when using the present invention, measurement can be performed with one test.

Further, in an existing nerve conduction test, because measurement of a portion between a measurement point and a stimulation point is performed with one or two electrodes, when an abnormality occurs in an intermediate nerve conduction portion, measurement should be minutely performed several times in order to search for a problem portion, but when using the present invention, an abnormal portion can be found through one test with an error by a coordinate gap.

Therefore, a characteristic of a nerve conduction test using the present invention is that it can accurately measure a nerve moving path due to many electrodes that can measure as well as nerve conduction with only one test and that it can accurately search for a portion having an abnormality in the nerve moving path.

By performing the electromyogram with in this way, several portions can be simultaneously measured.

Further, in a treatment method that causes specific muscle contraction like FES, by stimulating each coordinate of a pad using the present invention, after stimulation of another portion like electromyogram or nerve conduction measurement, by measuring a bio-electrical signal, in a method of searching for and again treating a stimulation portion of an accurate muscle in which specific muscle contraction most frequently occurs, by causing contraction that applies electrical stimulation to the portion, the treatment method is used for a treatment. The above method gives a change in a frequency and a wavelength of electrical stimulation to a treatment coordinate that simultaneously causes contraction, searches for a waveform having a largest treatment effect as a level reacting thereto through a biosignal measurement method, and performs a treatment using the frequency and the waveform. That is, with the above method, a biosignal such as a waveform and frequency strength of electrical stimulation corresponding to each muscle and a treatment of a patient is obtained and a treatment is performed according to the biosignal.

Figure 2:
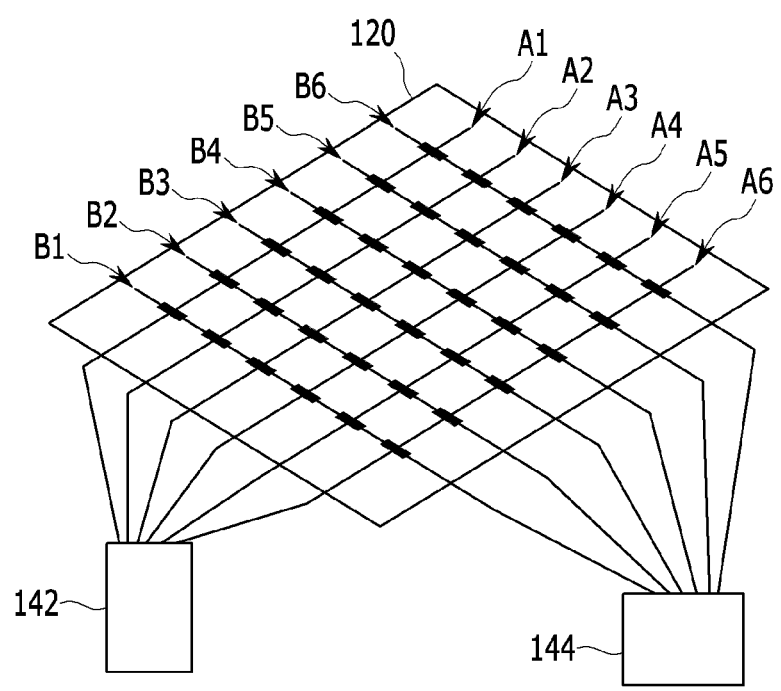
FIG. 2 is a schematic view illustrating operation of an electrical stimulation device according to an exemplary embodiment of the present invention.
Figure 3:
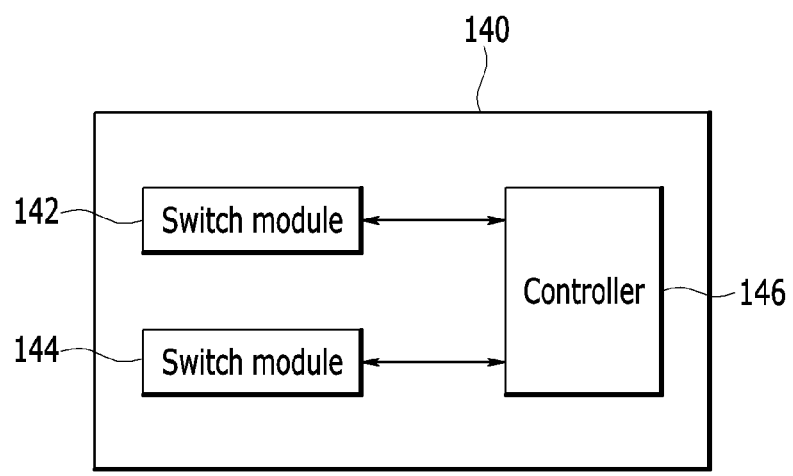
FIG. 3 is a block diagram illustrating a configuration of a control module of an electrical stimulation device according to an exemplary embodiment of the present invention.

FIG. 2 is a schematic view illustrating operation of an electrical stimulation device according to an exemplary embodiment of the present invention, and FIG. 3 is a block diagram illustrating a configuration of a control module of an electrical stimulation device according to an exemplary embodiment of the present invention.

Referring to FIG. 3, the control module 140 includes a switch module 142, a switch module 144, and a controller 146. The switch modules 142 and 144 perform a function of controlling on/off of power that is applied to an electrical wire, and the controller 146 controls the switch modules 142 and 144 to perform a function of controlling an entire operation of the bio-electrical signal measurement and electrical stimulation device 100 according to the present invention.

According to the present invention, by simultaneously measuring electromyogram or nerve conduction through an electrode, a large portion having a largest signal, a portion having an abnormal signal, or a treatment portion is recognized, and by applying an electrical signal having intensity and a frequency of a predetermined wave to the portion, after stimulation is applied, while gradually changing the waveform, the frequency, and the intensity, by repeating biosignal measurement, most effective stimulation is detected and thus continued stimulation is applied.

For muscle contraction, stimulation through a nerve is required, but it is difficult to perform the stimulation to a patient in which abnormality occurs in a muscle exercise due to abnormality in nerve conduction. Therefore, when a nerve signal is weak like a nerve paralysis patient, by directly applying stimulation to a corresponding muscle by amplifying the signal, muscle exercise may be caused. That is, by measuring specific nerve conduction, when a stimulation amount is a predetermined value or less, a micro-signal of a damaged nerve is measured, by recognizing an intention of a patient to use a muscle, the signal is amplified, and by applying electrical stimulation of a magnitude proportional to nerve stimulation to a muscle that the nerve controls, muscle contraction may be caused.

By promoting recovery of a combination exercise of a nerve and a muscle in a muscle remedial exercise through such a treatment, a remedial treatment can be performed more effectively than when performing only a muscle remedial treatment.

As shown in FIG. 2, in the biosignal measurement and electrical stimulation device according to the present invention, in the pad 120, horizontal electrical wires A1, A2, A3, A4, A5, and A6 are formed with a predetermined gap and vertical electrical wires B1, B2, B3, B4, B5, and B6 are formed with a predetermined gap to be orthogonal thereto.

The horizontal electrical wires A1-A6 are connected to the switch module 142, and the vertical electrical wires B1-B6 are connected to the switch module 144. The switch modules 142 and 144 each perform a function that controls on/off of power that is applied to the horizontal electrical wires A1-A6 and the vertical electrical wires B1-B6, measure a biosignal of a patient body portion at an intersection of each electrical wire with such operation, and generate electrical stimulation.

In this case, the horizontal electrical wires A1-A6 and the vertical electrical wires B1-B6 may be disposed at a predetermined gap or may be connected through a semiconductor element. When the horizontal electrical wires A1-A6 and the vertical electrical wires B1-B6 are disposed with a predetermined gap at an intersection point, the horizontal electrical wires A1-A6 and the vertical electrical wires B1-B6 may be disposed with a gap within approximately 5 cm. A predetermined gap may be variously changed according to a size of the pad 120 and a characteristic of a body portion, which is a treatment target.

In this case, measurement of a biosignal or generation of electrical stimulation may be performed by measuring a value of a current flowing by generating a potential difference in the horizontal electrical wires A1-A6 and the vertical electrical wires B1-B6, and a detailed description thereof is as follows.

When forming an electrode for measuring a biosignal, for example, after the switch module 142 turns on A1 by the control of the controller 146, the switch module 144 is sequentially turned on from B1 to Bn and thus a random measurement electrode is formed at the coordinates such that a biosignal may be measured, and by performing measurement up to An with this method, a biosignal of each of coordinates from a coordinate (A1, B1) to a coordinate (An, Bn) may be obtained.

As shown FIG. 2, at each intersection, an insulating material is disposed to enable the horizontal electrical wires A1-A6 and the vertical electrical wires B1-B6 to be electrically insulated from each other. In this case, horizontal electrical wires and vertical electrical wires may be disposed without a gap in a state of being insulated from each other with an insulating material, but it is preferable that the horizontal electrical wires and the vertical electrical wires are disposed to have a constant gap.

In this case, the constant gap may be set to various lengths, but may be formed to have a length of, for example, 1 mm. At the gap or the intersection portion, a conductive material such as gold for reducing resistance may be further disposed.

Particularly, when generating electrical stimulation, if a positive (+) voltage and a negative (−) voltage are applied to horizontal electrical wires and vertical electrical wires, respectively, the horizontal electrical wires and the vertical electrical wires are insulated by an insulating material and thus a current does not flow to skin of a patient, but when a potential difference of a predetermined threshold value or more is applied, a current flows to the skin of the patient, i.e., electrical stimulation is applied to the patient skin with such a method.

Figure 4:
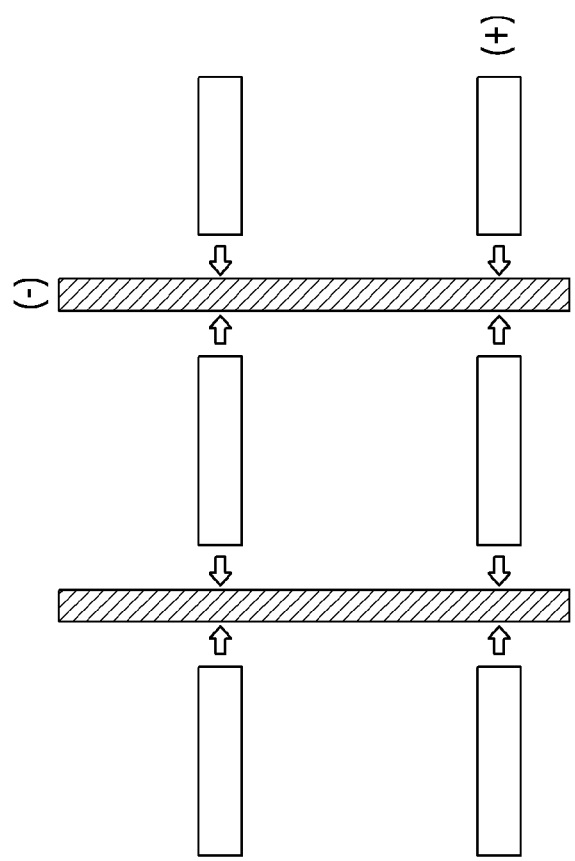
FIG. 4 is a diagram illustrating a structure of a pad according to a first exemplary embodiment of the present invention.

FIG. 4 is a conceptual diagram for the above content (i.e., FIG. 4 illustrates a structure of a pad according to a first exemplary embodiment). That is, as shown in FIG. 4, horizontal electrical wires and vertical electrical wires are disposed to intersect and are protected with an insulating material to maintain a state that is not short-circuited. In this case, in a horizontal electrical wire and a vertical electrical wire of an intersection portion, in order to expose a partial conductor, an insulator may be peeled off, and when a predetermined voltage or more is applied, a current may flow from a positive (+) electrode electrical wire to a negative (−) electrode electrical wire via skin.

In this case, as shown in FIG. 2, one pad 120 may be formed, but two pads may be formed. When one the pad 120 is formed, an outer edge portion of the pad 120 may be grounded.

When two pads are formed, an outer edge portion of each pad may be grounded, and the ground of each pad may be electrically connected to an inside electrical wire of the other pad. This is for a case of requiring the grounds to be separated by a predetermined distance when measuring a biosignal.

For example, upon measuring skin resistance, when measuring treatment coordinates of a left hand, a right hand becomes a reference point, and when searching for treatment points of the right hand, if the left hand becomes a reference point, a distance between a different point of the back of the hand and a reference point is constant and thus when measuring each skin resistance, an error according to a distance between reference points reduces. When measuring skin resistance of the back of the right hand, by fixing one pad to the back of the left hand and contacting the other pad with the back of the right hand, measurement may be performed.

Further, when measuring electromyogram and nerve conduction, the electromyogram and nerve conduction may be measured with a line (vertical or horizontal) in an advancing direction of an electrical signal of the nerve conduction and the electromyogram.

That is, as shown in FIG. 2, a current is applied through wires A and B that are located at a skin contact surface, and in this case, the measurement method takes a type that measures a specific point of skin, as in a resistance measurement device. Because a current is applied in a direction having a shortest distance and lowest resistance, when measuring a signal such as electrical resistance, a location (point to measure) of a shortest distance between A and B may be measured.

Therefore, in FIG. 2, an intersecting portion of wires A and B becomes a measuring point, and when applying electrical stimulation, while a current is applied in the intersection portion of A and B with the same principle, electrical stimulation is applied to a body portion.

Figure 5A:
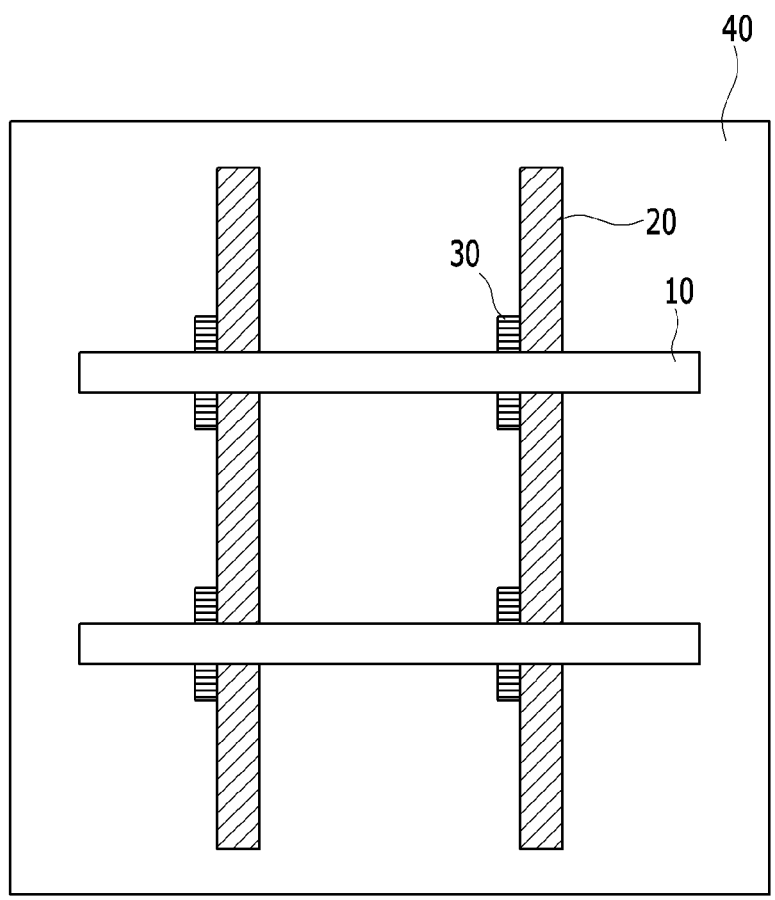
FIGS. 5A to 5C are diagrams illustrating a structure of a pad according to a second exemplary embodiment of the present invention.
Figure 5B:
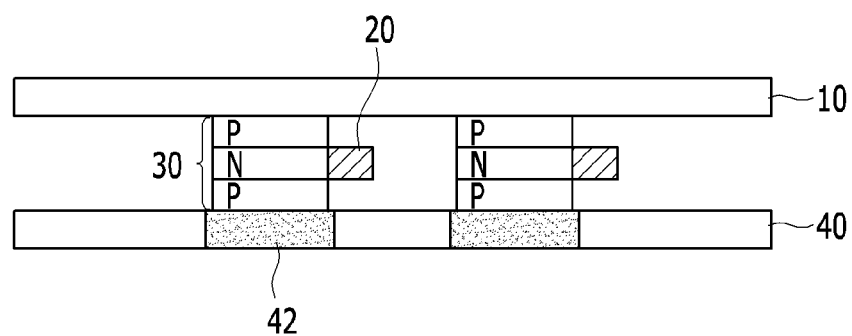
Figure 5C:
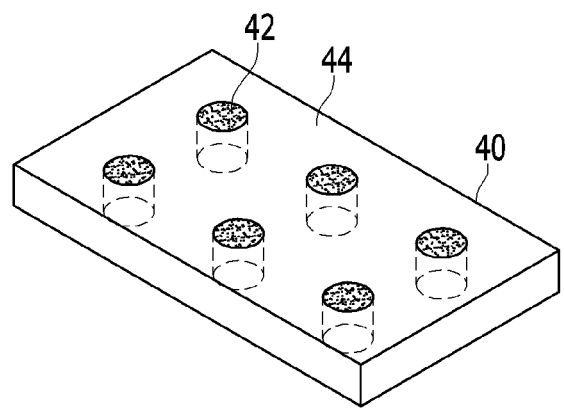

As shown in FIGS. 5A to 5C, another pad may include a structure using a semiconductor element (i.e., FIGS. 5A to 5C illustrate a structure of a pad according to a second exemplary embodiment).

Referring to FIG. 5A, in a skin cohesion pad 40, horizontal electrical wires 10 and vertical electrical wires 20 are disposed to intersect, and the horizontal electrical wires 10 are connected to the vertical electrical wire 20 through the PNP-type transistor 30.

FIG. 5B illustrates a cross-sectional view of a side surface of a structure of FIG. 5A. That is, at the top, the horizontal electrical wire 10 is formed, in a lower portion of the horizontal electrical wire 10, the PNP-type transistor 30 is disposed, and a lower portion of the PNP-type transistor 30 contacts the skin cohesion pad 40.

FIG. 5C is a diagram illustrating the skin cohesion pad 40, and the skin cohesion pad 40 is formed with a conductive portion 42 and a non-conductive portion 44. The conductive portion 42 is formed in plural at a location corresponding to a lower portion of the PNP-type transistor 30, and may be formed with a conductive cohesion gel or other conductive materials. The non-conductive portion 44 is made of a non-conductive material.

An upper p-type semiconductor of the PNP-type transistor 30 corresponds to an emitter, an intermediate n-type semiconductor corresponds to a base, and a low p-type semiconductor corresponds to a collector. The horizontal electrical wire 10 is bonded to an upper portion of the upper p-type semiconductor, and the vertical electrical wire 20 is bonded to the intermediate base. In the transistor, as a current flows to the base, a current flows from the emitter in a direction of the collector.

Therefore, when a predetermined current flows to horizontal electrical wires that are connected to the emitter, if a current does not flow to vertical electrical wires that are connected to the base, a current does not flow in a direction of skin that is connected to the collector, and when a current flows to the vertical electrical wire, a current flows in a direction of skin that is connected to the collector.

When desired coordinates are (A2, B10) (where A indicates a horizontal electrical wire, B indicates a vertical electrical wire, and the number is the serial number of a plurality of electrical wires), a current of a predetermined voltage or more is applied to A2, and when a current flows to B10, a current flows to the coordinates (A2, B10).

Such a method may be used even when simultaneously stimulating several coordinate sets. That is, when stimulating coordinates (A2, B10), (A2, B15), (A5, B15), and (A3 and B5), a current is applied to the horizontal electrical wires A2, A3, and A5, and when a current is applied to the vertical electrical wires B5, B10, and B15, a current may flow to the coordinates.

The method enables a current to flow toward the skin, but may enable a current to flow from the skin side toward an electrical wire when using an NPN-type semiconductor.

In the foregoing description, a PNP-type semiconductor is illustrated, but in order to enable a current to flow toward the skin or to enable a current to flow from the skin side toward an electrical wire, an NPN-type transistor and a PNP-type transistor may each be used or may be simultaneously used, and another semiconductor element may be used.

When body information is acquired, the control module 140 according to the present invention may apply a voltage of 1-10 V and a current of 10-50 µA, and when electrical stimulation occurs, the control module 140 may apply a voltage of 50-100 V and a current of 5-20 mA.

In the foregoing exemplary embodiment, measurement of a biosignal by enabling a current to flow by generating a potential difference or controlling a semiconductor element at an intersection of the control module 140 of the present invention has been described, but the control module 140 may measure a current without generating a potential difference or enabling a current to flow at an intersection, thereby measuring a biosignal. That is, the control module 140 may include an ammeter to measure a microcurrent flowing to the skin.

Therefore, such a method may be applied to an electrocardiogram (ECG) and an electroencephalogram (EEG) that measure bio-electrical signals such as a microcurrent and a waveform occurring in a human body.

Hereinafter, a method in which an electrical stimulation device according to the present invention acquires a biosignal of a patient and generates electrical stimulation will be described in detail with reference to FIG. 6.

Figure 6:
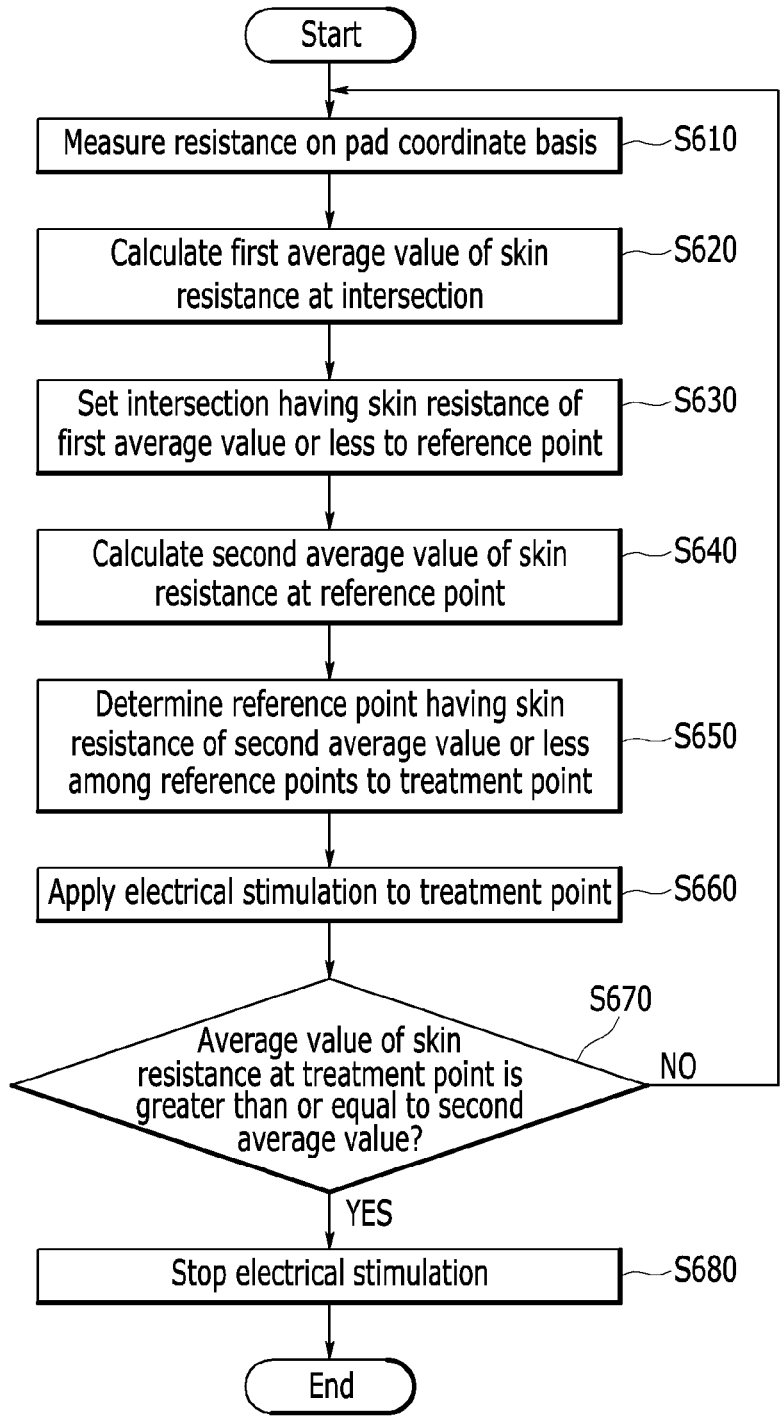
FIG. 6 is a flowchart illustrating operation of an electrical stimulation device according to an exemplary embodiment of the present invention.

FIG. 6 is a flowchart illustrating operation of an electrical stimulation device according to an exemplary embodiment of the present invention.

First, the pad 120 is put on a specific body portion of a patient and a biosignal of each intersection is measured (S610). As described above, the horizontal electrical wires A1-A6 and the vertical electrical wires B1-B6 are disposed at a predetermined gap, and when the horizontal electrical wires A1-A6 and the vertical electrical wires B1-B6 are disposed in this way, a biosignal (e.g., resistance) of each coordinate intersection (An, Bn) of the skin may be obtained and electrical stimulation may be applied to each coordinate set.

For example, after a switch of the horizontal electrical wire A5 and the vertical electrical wire B1 is turned on, when resistance is measured using the horizontal electrical wire and vertical electrical wire as terminals, a point having different resistance values may exist at a periphery of the coordinates. That is, a point in which a skin electrical resistance value is different becomes an electrical stimulation point.

An example of searching for a point in which skin electrical resistance is different has been described, but as described above, the present invention may be used for electromyogram and nerve conduction measurement, using an instrument that measures a potential difference of electricity and electrical stimulation of a muscle.

At step 610, when skin resistance is measured on an entire pad coordinate basis, an entire impedance average value, i.e., a first average value of skin resistance of an intersection, is calculated (S620). Thereafter, among intersections, an intersection having a skin resistance value of a first average value or less is set as a reference point (S630).

At a reference point, a second average value of skin resistance is calculated (S640). In this case, among reference points, a reference point having skin resistance of a second average value or less is determined as a treatment point (S650) and electrical stimulation occurs at the treatment point (S660).

In this case, as a method of generating electrical stimulation at the treatment point, a method of sequentially generating electrical stimulation on each coordinate basis may be used, and a detailed method thereof is as follows.

Referring to FIG. 2, intersections of the horizontal electrical wires A1-A6 and the vertical electrical wires B1-B6 exist, and within a coordinate range that does not overlap, such as (A1, B1), (A2, B2), and (A3, B3), electrical stimulation may occur simultaneously. When five treatment coordinates exist, a method of simultaneously applying electrical stimulation to treatment coordinates among the five treatment coordinates and applying electrical stimulation to the remaining treatment coordinates may be used, or a method of sequentially applying electrical stimulation to each treatment point from the first time may be used. Alternatively, a method of alternately applying electrical stimulation to the predetermined number of treatment points with a random method may be used.

When applying electrical stimulation to a treatment point in this way, a resistance value of the treatment point gradually approaches an average value further from a first resistance value, and when a resistance value of the treatment point approaches a second average value, it is regarded that the treatment is complete and thus it is no longer necessary to apply electrical stimulation.

Therefore, it is determined whether an entire skin resistance value at the treatment point is greater than or equal to the second average value (S670), and if the entire skin resistance value at the treatment point is greater than or equal to the second average value, electrical stimulation is stopped (S680).

If the entire skin resistance value at the treatment point is smaller than the second average value, the process returns to step 610, and skin resistance on a pad coordinate basis is measured again and the foregoing steps are repeated. In a treatment process of this method, a new treatment point may appear, and even in such a case, in order to easily and completely perform a treatment, treatment efficiency may be adjusted by adjusting a stimulation amount and a stimulation time.

In this case, a method of not returning to step 610 and applying electrical stimulation until the skin resistance value at a treatment point arrives at the second average value at step 660 may be performed.

However, even if a treatment is complete, i.e., even if an impedance value of an entire treatment point arrives at an average value, an average value of each coordinate, a coordinate (treatment point) of an average value or less, and a coordinate (treatment point) in which electrical resistance is an average value or more exist. However, at this time, a difference of an impedance value of a coordinate is reduced a lot and thus is reduced further than a difference between an average value of a first treatment point and an average value of a treatment point. Therefore, when an impedance value is reduced to a predetermined difference value or less (e.g., when first two values are reduced to 50% or less of the difference value), it is recognized that treatment of all treatment points is complete and the treatment may be terminated.

Figure 7:
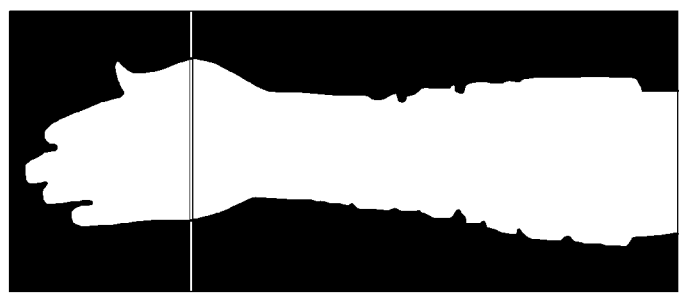
FIG. 7 is a diagram illustrating distribution of a skin resistance value of the inside of an arm with a color.

FIG. 7 is a diagram illustrating distribution of a skin resistance value of the inside of an arm with a color. According to a bio-electrical signal measurement and electrical stimulation apparatus using a pad having a mesh-type structure according to the present invention, as shown in FIG. 7, while a bio-electrical signal such as skin resistance of each point can be simultaneously measured, electrical stimulation can be applied to a necessary location.

In the foregoing description, an exemplary embodiment of the present invention has been described in detail with reference to the drawings. However, the exemplary embodiment is described for explaining the present invention and the present invention is not limited thereto. While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The present invention may be used in a production field of a biosignal measurement and electrical stimulation device.

The invention claimed is:

1. A biosignal measurement and electrical stimulation device, comprising:
   a pad including a plurality of horizontal electrical wires and a plurality of vertical electrical wires at a plurality of intersecting locations; and
   a control module that is electrically connected to the pad adapted to acquire body state information of a patient by measuring a biosignal at the plurality of intersecting locations,
   wherein the biosignal represents skin resistance, and
   wherein the control module calculates a first average value of the skin resistance measured at the plurality of intersecting locations, selects reference points having skin resistance of the first average value or less, calculates a second average value of skin resistance of the reference points, determines a treatment point having skin resistance of the second average value or less, and generates electrical stimulation at the treatment point.

2. The biosignal measurement and electrical stimulation device of claim 1, wherein the biosignal measured by the control module is an electrical signal flowing to the plurality of intersecting locations.

3. The biosignal measurement and electrical stimulation device of claim 2, wherein the horizontal electrical wires are separated from the vertical electrical wires at each of the plurality of intersecting locations with a gap, and
a predetermined potential difference between the horizontal electrical wires and the vertical electrical wires connected to the plurality of intersecting locations creates a current flow to generate the electrical stimulation.

4. The biosignal measurement and electrical stimulation device of claim 3, further comprising an insulating material to insulate the horizontal and vertical electrical wires at the plurality of intersecting locations, and
a conductive material disposed at the gap for reducing resistance when generating the electrical stimulation.

5. The biosignal measurement and electrical stimulation device of claim 2, further comprising a semiconductor element disposed at each of the plurality of intersecting locations between the horizontal electrical wires and the vertical electrical wires, and
the control module controls the semiconductor element to create the current flow at a desired intersecting location among the plurality of intersecting locations and to generate electrical stimulation at the desired intersecting location.

6. The biosignal measurement and electrical stimulation device of claim 1, wherein the pad comprises a plurality of intersection electrodes formed of a conductor or a conductive bonding gel disposed at the intersecting locations and a periphery part of the intersection electrodes formed of a non-conductive bonding fabric or a non-conductive bonding gel.

7. The biosignal measurement and electrical stimulation device of claim 1, further comprising perforations for air permeability in the pad.

8. The biosignal measurement and electrical stimulation device of claim 1, wherein the pad has a shape of a circle, an oval, a square, a rectangle, a glove, a sock, a band, or a cap.

9. The biosignal measurement and electrical stimulation device of claim 1, wherein the control module stops the electrical stimulation at a corresponding treatment point when the skin resistance value at the corresponding treatment point arrives at the second average value.

* * * * *